United States Patent [19]
Mohr et al.

[11] Patent Number: 5,519,225
[45] Date of Patent: *May 21, 1996

[54] SYSTEM AND METHOD FOR USING A DUAL MODALITY DETECTOR FOR INSPECTING OBJECTS

[75] Inventors: Gregory A. Mohr, Scotia; Robert S. Gilmore, Burnt Hills, both of N.Y.; Gerald B. Nightingale, Westchester; Thomas W. Birdwell, Middleton, both of Ohio

[73] Assignee: General Electric Company, Schenectady, N.Y.

[*] Notice: The term of this patent shall not extend beyond the expiration date of Pat. No. 5,489,781.

[21] Appl. No.: 317,049

[22] Filed: Oct. 3, 1994

[51] Int. Cl.$^6$ .................... G01T 1/185; G01T 3/00; G01N 23/09
[52] U.S. Cl. .................... 250/390.02; 250/385.1; 378/63
[58] Field of Search .................... 250/374, 385.1, 250/390.01, 390.02; 378/63

[56] References Cited

U.S. PATENT DOCUMENTS

| | | | |
|---|---|---|---|
| 4,570,071 | 2/1986 | Sippel et al. | 250/374 |
| 4,587,555 | 5/1986 | Carollo et al. | 250/390.02 |
| 4,864,142 | 9/1989 | Gomberg | 250/390.02 |

FOREIGN PATENT DOCUMENTS

| | | | |
|---|---|---|---|
| 2557092 | 7/1977 | Germany | 250/390.02 |
| 113842 | 7/1983 | Japan | 250/39.02 |

*Primary Examiner*—Carolyn E. Fields
*Attorney, Agent, or Firm*—David C. Goldman; Paul R. Webb, II

[57] ABSTRACT

A system and method for using the detector to differentiate neutron attenuating material from high x-ray attenuating material in an object. The inspection system is used to detect the presence of nitride in titanium sponge nuggets or residual core material in a hollow-cast turbine engine blades. The inspection system uses a dual radiation source to alternately emit neutrons and x-rays or gamma rays at the object under inspection. A dual modality gas ionization detector detects the radiation passing through the object and sends the detected radiation to a processing means for image generation. The generated image is displayed on a display, enabling objects formed with low and high attenuating material to be distinguished.

14 Claims, 2 Drawing Sheets

SYSTEM AND METHOD FOR USING A DUAL MODALITY DETECTOR FOR INSPECTING OBJECTS

CROSS REFERENCE TO RELATED PATENT APPLICATIONS

This application is related to application entitled "A Dual Modality Detector," U.S. patent application Ser. No. 08/317,051 filed concurrently herewith and assigned to the same assignee as the present invention.

BACKGROUND OF THE INVENTION

The present invention relates generally to radiography, and more particularly to using radiographic inspection for examining objects.

Radiographic inspection generally involves discriminating an amount of penetrating radiation (i.e., x-ray or gamma ray) that is transmitted along different paths through an object. Current radiographic inspection methods are capable of only detecting the total amount of radiation being transmitted along a path through the object and not the amount of radiation being transmitted at each of the individual locations that comprise the path. For example, in a conventional x-ray radiographic system, a sheet of film is used to detect the x-rays being transmitted through an object along the paths that arise between each region of the sheet of film and a x-ray source. In regions corresponding to paths that contain relatively large amounts of highly attenuating material, the film intercepts few transmitted x-rays, whereas for paths containing small amounts of less attenuating materials, the film is heavily exposed. Since the sheet of film is sensitive to the total of summed contributions to the beam attenuation along each path, it is very difficult to discriminate between paths containing a small amount of highly attenuating material and paths with a correspondingly greater amount of less attenuating material.

The lack of discrimination in conventional radiographic methods makes detection of certain types of flaws extremely difficult. In particular, it is very difficult to detect defects in objects that are characterized by having small amounts of slightly attenuating materials combined with an overall background of highly attenuating material. Examples of such inspection problems are present in x-ray radiographic detection of nitrogen contamination of titanium, which is believed to be the underlying cause for hard α defects, and the detection of unremoved ceramic core material in cast nickel-alloy turbine blades, which is believed to be responsible for certain types of blade failure during operation. However, the contaminants in both these examples attenuate neutrons at significantly different levels then the base materials. If the titanium nuggets and turbine blades contain small amounts of neutron attenuating material, it is very important to be able detect nuggets and blades which have the neutron attenuating material. In either case, conventional x-ray radiographic detection is unable to discriminate the neutron attenuating material from the large x-ray attenuation material.

One possible solution to the above problems is to use computed tomography (CT), which measures the local attenuation coefficient in an image plane. However, CT requires a large number of radiographic exposures for each image plane and extensive computation for reconstructing the image. Other disadvantages in using CT for inspections are that it is expensive and time-consuming, especially if many image slices are required to adequately sample the object volume.

Another technique used to overcome the problems associated with conventional radiographic methods is to use dual-energy x-ray methods to discriminate between material properties. Dual energy x-ray methods attempt to measure the amount of energy that is absorbed and scattered. Determining the separate contributions between absorption and scattering requires a significant amount of processing, and is generally very difficult to do effectively with conventional x-ray sources. In order to overcome this problem, some dual energy methods have replaced the variable energy x-ray source with gamma ray sources. However, gamma ray sources are usually weaker than x-ray sources, resulting in greater signal to noise effects. A problem common to both the x-ray source and the gamma ray source dual-energy method is that they are not sensitive to neutrons.

Another technique that has been used is to replace the radiographic film with gas ionization detectors filled with $BF_3$, $^3He$ or Xe. An example of a gas ionization detector filled with Xe is disclosed in U.S. Pat. No. 4,570,071. The problem with these types of gas ionization detectors are that they are sensitive either to only x-rays or gamma rays or only to neutrons and not sensitive to both x-rays or gamma rays and neutrons.

SUMMARY OF THE INVENTION

An object of the present invention is to use a dual modality gas ionization detector in industrial inspection systems and methods for detecting, characterizing, and differentiating small amounts of neutron attenuating materials in objects composed primarily of materials with large x-ray attenuation material.

Thus, in accordance with one embodiment of the present invention, there is provided a system for inspecting an object. The system comprises a dual radiation source for alternately irradiating the object with neutrons and x-rays or gamma rays. A dually sensitive detector measures both types of radiation alternately passing through the object. A processing means processes the detected radiation into an image differentiating small amounts of neutron attenuating material from large amounts of x-ray attenuating material. A display means displays the image generated from the processing means.

Still in accordance with a second embodiment of the present invention, there is provided a method for inspecting an object with a dual radiation source, a dual modality gas ionization detector, an image generator, and a display. The method comprises the steps of alternately irradiating the object with neutrons and x-rays or gamma rays. The alternating radiation passing through the object is then measured. The detected radiation is processed into an image that differentiates small amounts of neutron attenuating material from large amounts of x-ray attenuating material. The image is then displayed.

While the present invention will hereinafter be described in connection with a preferred embodiment and a system and method of use, it will be understood that it is not intended to limit the invention to this embodiment. Instead, it is intended to cover all alternatives, modifications and equivalents as may be included within the spirit and scope of the present invention as defined by the appended claims.

DETAILED DESCRIPTION OF THE PRESENT INVENTION

Figure 1:
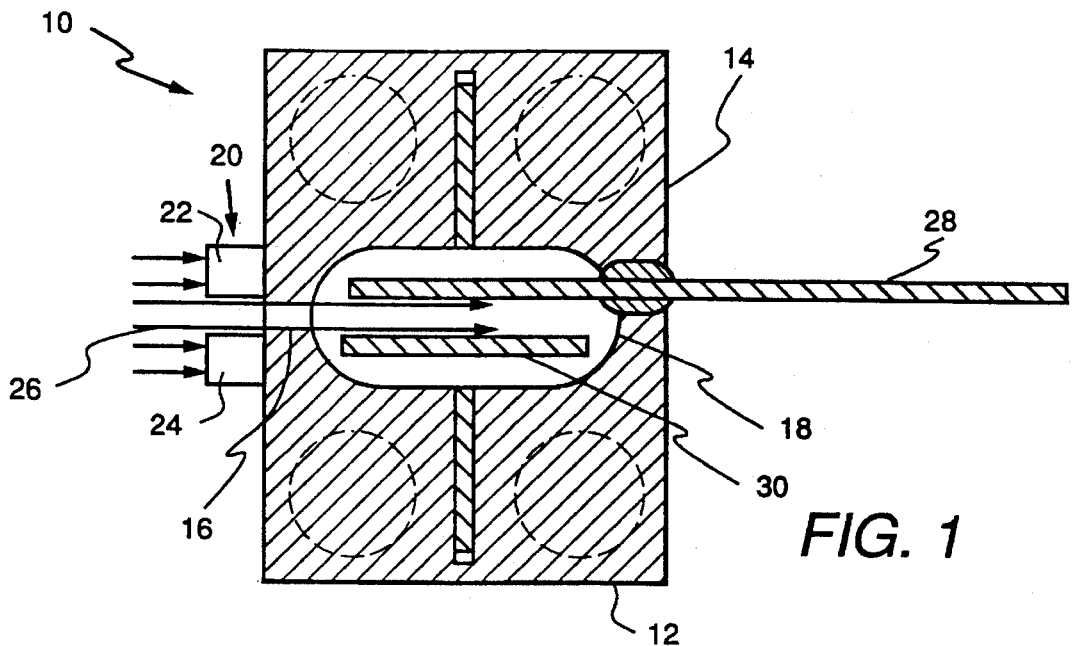
FIG. 1 shows a cross-sectional view of the dual modality gas ionization detector used in the present invention.

FIG. 1 is a cross-sectional view of a dual modality gas ionization detector 10 used in the present invention. The detector is disclosed in the commonly assigned, co-pending, and concurrently filed application entitled "A Dual Modality Detector," U.S. patent application Ser. No. 08/317,051. The detector includes a generally-rectangular housing 12 made of a metal or metal alloy having an end plate 14 at one end and a window 16 for transmitting incident neutrons and x-rays or gamma rays at an opposite end. The window is constructed of a material which is permeable to neutrons and x-rays or gamma rays such as aluminum. The window is preferably a plano-concave aluminum lens that permits neutrons and x-rays or gamma rays to enter the housing. Inside the housing is an ionization chamber 18 filled with high pressure gases such as $^3$He and Xe. The $^3$He and Xe gases are used in the ionization chamber to detect the neutron and x-ray or gamma ray fluxes incident on the ionization detector. In the preferred embodiment, the mixture of Xe gas and $^3$He gas is formed from a partial pressure of $^3$He having a range of about 0.5 to about 2 atmospheres and a partial pressure of Xe having a range of about 50 to about 75 atmospheres. In another embodiment, $BF_3$ can be used in place of $^3$He. A collimator 20 which comprises two bars 22 and 24 made from tungsten, gadolinium, or the like, define a slit 26 between the parallel bars. The neutrons and x-rays or gamma rays entering the chamber are collimated to be substantially parallel and travel as a thin beam into the chamber. An array of electrodes 28 extending through the housing end plate into the chamber are positioned parallel to the entering thin sheet of radiation. Also, in the chamber is an electrically conductive plate 30, which is substantially parallel to the array of electrodes.

In operation, radiation enters the chamber through the collimator and the window and interacts with the $^3$He and Xe gases to produce secondary ionization charges. Since the electrodes are maintained at a potential difference relative to the electrically conductive plate 30, there exists an electric field which separates negative electrons from positively charged ions, and accelerates the charged particles toward an electrode. The charges are then detected by the array of electrodes 28. Further discussion of the gas ionization detector and its operation are provided in U.S. Pat. No. 4,570,071, which is incorporated herein by reference.

The ratiometric detection used by the dual modality gas ionization detector is based on the theory that the attenuation of ideal beams of either neutrons or photons from x-rays or gamma rays passing through an object made from homogeneous material is described by the following relation:

$$I = I_0 e^{-\alpha L}, \quad (1)$$

wherein I is the intensity of the beam after passing through the object, $I_0$ is the incident beam intensity, $\alpha$ is the linear attenuation coefficient of the object material for the type of radiation, and L is the path length of the beam through the object. The transmitted fraction of the beam, T, is the ratio of I over $I_0$. Thus, the transmitted fraction of the beam is measured by recording the detector output signal in the absence of the object, which is proportional to $I_0$, with the part in the beam, which is proportional to I. Then one result is divided by the other result to obtain T.

By translating the object relative to the dual modality detector in the direction perpendicular to both the beam and the detector array, a two-dimensional mapping of transmission is obtained by using a processing means and a display. The resulting digital radiograph resembles a conventional film radiograph. For inspections of normally homogeneous material objects, the T data is logarithmically transformed as $$-\ln T = -\ln \frac{I}{I_0} = -\ln(e^{-\alpha L}) = \alpha L, \quad (2)$$

which obtains a mapping or image with pixel values that are proportional to the amount of material penetrated along each path between source and detector elements.

One of the central features of the present invention involves forming an image or mapping of the ratio of both logarithmically transformed measures in the form $$R = \frac{-\ln T_x}{-\ln T_n} = \frac{\alpha_x L}{\alpha_n L} = \frac{\alpha_x}{\alpha_n}, \quad (3)$$

wherein subscripts n and x refer to neutron and x-ray measurements respectively. The measurement of R provides a constant value characteristic of the material in the beam path that does not depend on the amount of material present in the beam path. However, if a small defect composed of a different material is present in the object under inspection, an image R demonstrates a variation from the constant background level that depend on the amount and type of defect material present.

Since R is independent of the amount of material, this method permits inspection of foreign object defects and inclusions even in irregularly shaped objects such as titanium sponge nuggets, turbine blades or the like. Nuggets with spatially localized nitrogen or oxygen bearing inclusions will produce R-images with distinct regions of variations different from the characteristic value for titanium. Nuggets that have an overall contamination will yield images having a marked thickness variation due to the presence of multiple materials.

The ratiometric method can also be extended to more sophisticated transformations than the logarithmic approached outlined above. The attenuation of polychromatic x-ray beams, for instance, does not follow a strict exponential dependence. However, more correct relations between measured transmittances and $\alpha_n, \alpha_x$, and L can be used for identifying anomalous values of R as a function of $I_n$ and $I_x$, similarly characterizing the presence of foreign materials.

Figure 2:
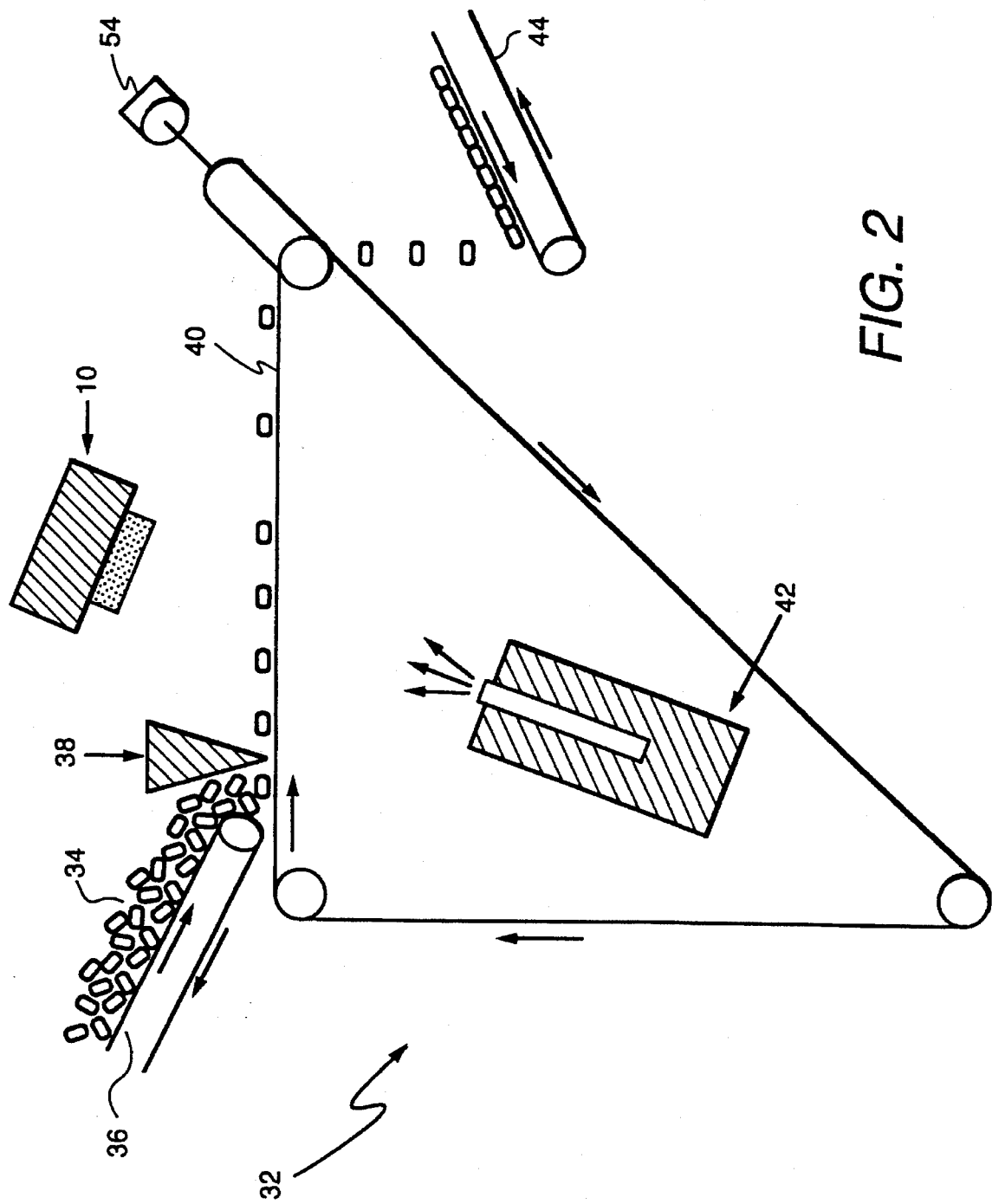
FIG. 2 shows a diagram of an inspection system using the dual modality gas ionization detector to detect nitrided titanium sponge nuggets.

As mentioned earlier, the dual modality gas ionization detector 10 is suitable for detecting, characterizing, or differentiating small amounts of neutron attenuating materials in objects composed primarily of materials of large x-ray attenuation material. In particular, the dual modality gas ionization detector can be used to detect defects such as nitrogen contaminations present in titanium sponge nuggets and residual core material present in hollow-cast turbine blades. FIG. 2 shows a diagram of an inspection system 32 for detecting nitrided titanium sponge nuggets. Although the inspection system is described for contaminated titanium nuggets, it can be used for various applications that require detecting, characterizing, or differentiating small amounts of neutron attenuating materials in objects composed primarily of materials having large x-ray attenuation.

In FIG. 2, a plurality of titanium sponge nuggets 34 are transported down a first conveyor belt 36 to a skimming weir 38 wherein the nuggets are arranged into a single layer on a second conveyor belt 40. The nuggets are moved past a dual radiation source 42 which alternately pulses neutrons and x-rays or gamma rays at the nuggets. The second conveyor belt 40 is preferably made from material with very low attenuation of neutrons and x-rays or from thin sheets of pure titanium. A combination of alternately activated ion-beam neutron generators and conventional x-ray tubes is one example of a dual radiation source that is within the realm of the present invention. The dual modality gas ionization detector 10 measures the transmissivity of the alternating radiation passing through the nuggets. Separate transmission could also be achieved by displacing the dual modality gas ionization detector at either an angle or a position where the collimator in the detector alternately rejects the neutron and x-ray or gamma ray beams from separate radiation sources. If controlled radiation sources were not used, then another possibility is to use a mechanical shutter device such as a rotating disk composed of alternating segments of x-ray or gamma ray and neutron attenuating materials between the dual radiation source 42 and the dual modality gas ionization detector 10. A shutter would permit rapid alteration between neutrons while maintaining appropriate static alignment of the beams and the detector device. Locations of the dual radiation source 42 and the dual modality gas ionization detector are not limited to the positions shown in FIG. 2 and 3 and can be arranged in a manner that provides sufficient room for placement of physically large radiation sources.

Defective or nitride contaminated nuggets are detected by connecting the dual modality gas ionization detector 10 to an image generator 46. The image generator is shown connected to the detector in FIG. 3. The image generator includes an analog to digital converter (ADC) 48, a processing means 50, and an image display device 52. The ADC converts the detected radiation from the dual modality gas ionization detector to digital signals which are sent to the processing means. The processing means also receives positional information from an encoder 54 on the position of the dual radiation source 42, the dual modality gas ionization detector 10, and the second conveyor belt 40. The resulting positional information is used by the processing means to synchronize the digital output signals from the ADC with the radiation (i.e. neutrons and x-rays or gamma rays) being emitted from the dual radiation source 42. The synchronization enables two-dimensional inspection images to be generated as the nuggets 34 are continuously moved through alternating beams of radiation, assuming that the dual modality gas ionization detector uses a linear geometry detector. If a two-dimensional detector array is used instead, then the second conveyor belt 40 can be incrementally advanced through the detector's 10 field of view, and each segment being alternately irradiated with neutrons and x-rays or gamma rays. In either case, digital image representations of the material properties of nuggets is produced in near-real time.

Figure 3:
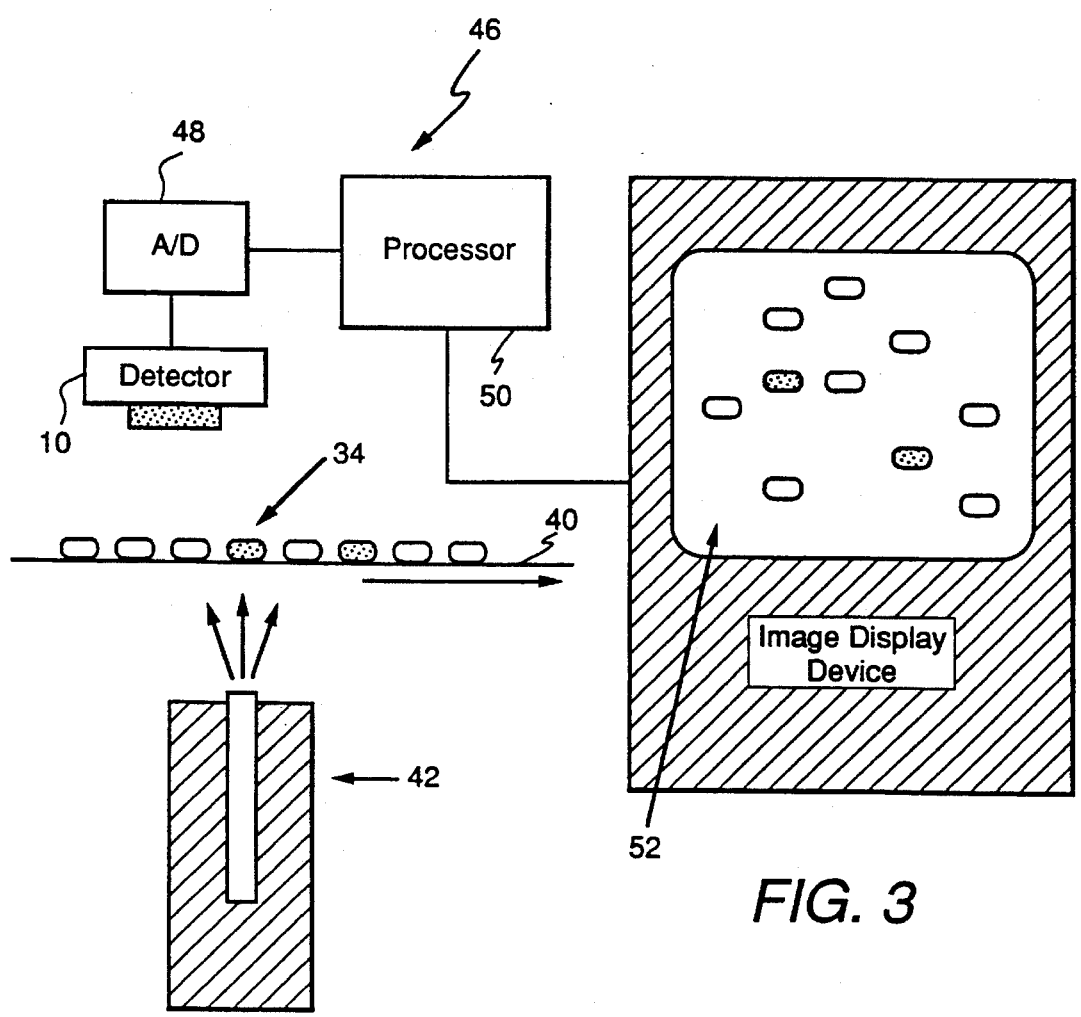
FIG. 3 shows a diagram of the inspection system used with an image generator and display.

The digital image representations provide different ratiometric signals for nuggets contaminated with nitride as compared to uncontaminated nuggets. The distinction between contaminated and uncontaminated nuggets is readily discernible from the image display device 52. In FIG. 3 the nuggets contaminated with nitride are shown in black. The contaminated nuggets can also be identified by having the processing means 50 perform an automatic feature identification routine on the digital data sent from the ADC. If any nugget 34 is identified as being contaminated with nitride, it is removed manually or mechanically. After the defective nuggets have been removed, the remaining nuggets are transported to a third conveyor belt 44 for further processing.

It is therefore apparent that there has been provided in accordance with the present invention, a system and method for using a gas ionization detector to detect low attenuating material from high attenuating material in an object that fully satisfy the aims, advantages and objectives hereinbefore set forth. The invention has been described with reference to several embodiments, however, it will be appreciated that variations and modifications can be effected by a person of ordinary skill in the art without departing from the scope of the invention.

We claim:

1. A system for inspecting an object, the system comprising:

a dual radiation source for alternately irradiating the object with neutrons and x-rays or gamma rays;

a dual modality detector for measuring the alternating radiation passing through the object, the detector detecting small amounts of neutron attenuating material from large amounts of x-ray attenuation material;

means for processing the detected radiation into an image differentiating the small amounts of neutron attenuating material from the large amounts of x-ray attenuation material, the processing means using a ratiometric procedure for detecting small neutron-attenuation inclusions in the object, the ratiometric procedure determining a ratiometric quantity R for various regions of the object, the ratiometric quantity R approximating the ratio:

$$R = \alpha_x / \alpha_n,$$

where $\alpha_x$ is the linear attenuation coefficient of the object for x-rays and $\Delta_n$ is the linear attenuation coefficient of the object for neutrons; and means for displaying the image generated from the processing means.

2. The system according to claim 1, wherein the processing means maps neutron and photon transmissivities of radiation passing through the object along each path between the dual radiation source and the dual modality detector.

3. The system according to claim 1, further comprising means for transporting the object relative to the dual modality detector, the object being in a direction perpendicular to both the detector and the radiation being emitted from the dual radiation source.

4. The system according to claim 3, further comprising means for encoding positions of the dual radiation source, the dual modality detector, and the transporting means, the positional information being used to synchronize detected radiation signals from the dual modality detector.

5. The system according to claim 1, wherein the image includes a plurality of pixel values each being proportional to an amount of material penetrated along an irradiation path between the dual radiation source and the dual modality detector.

6. The system according to claim 1, wherein the image is generated in real-time.

7. The system according to claim 1, further comprising means for removing the object if an impurity or defect is detected.

8. A method for inspecting an object with a dual radiation source, a dual modality gas ionization detector, an image generator and a display, the method comprising the steps off alternately irradiating the object with neutrons and x-rays or gamma rays;

detecting the alternating radiation passing through the object;

processing the detected radiation into an image differentiating small amounts of neutron attenuating material from large amounts of x-ray attenuating material, the processing step includes using a ratiometric procedure for detecting small neutron-attenuation inclusions in the object, the ratiometric procedure determining a ratiometric quantity R for various regions of the object, the ratiometric quantity R approximating the ratio:

$$R=\alpha_x/\alpha_n,$$

where $\alpha_x$ is the linear attenuation coefficient of the object for x-rays and $\Delta_n$ is the linear attenuation coefficient of the object for neutrons; and displaying the image.

9. The method according to claim 8, wherein the step of processing includes mapping neutron and photon transmissivities of radiation passing through the object along each path between the dual radiation source and the dual modality detector.

10. The method according to claim 8, further comprising the step of transporting the object relative to the dual modality detector, the object being in a direction perpendicular to both the dual modality detector and the radiation being emitted from the dual radiation source.

11. The method according to claim 8, wherein the image includes a plurality of pixel values each being proportional to an amount of material penetrated along an irradiation path between the dual radiation source and the dual modality detector.

12. The method according to claim 8, wherein the object is a titanium sponge nugget.

13. The method according to claim 8, further comprising the step of encoding positions of the dual radiation source and the dual modality detector, the positional information being used to synchronize detected radiation signals from the dual modality detector.

14. The method according to claim 8, further comprising the step of removing the object if an impurity or defect is detected.

* * * * *